(12) United States Patent
Berti et al.

(10) Patent No.: US 10,349,929 B2
(45) Date of Patent: Jul. 16, 2019

(54) CANNULA WITH CAP

(71) Applicant: Medos International Sarl, Le Locle (CH)

(72) Inventors: Stefano Berti, Quito (EC); Benjamin Cleveland, Milford, MA (US); Mehmet Z. Sengun, Canton, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 0 days.

(21) Appl. No.: 15/469,003

(22) Filed: Mar. 24, 2017

(65) Prior Publication Data

US 2018/0271508 A1 Sep. 27, 2018

(51) Int. Cl.
| | |
|---|---|
| *A61B 1/32* | (2006.01) |
| *A61B 17/02* | (2006.01) |
| *A61B 17/04* | (2006.01) |
| *A61B 17/34* | (2006.01) |
| *A61B 17/00* | (2006.01) |

(52) U.S. Cl.
CPC ...... *A61B 17/0218* (2013.01); *A61B 17/0401* (2013.01); *A61B 17/3421* (2013.01); *A61B 2017/00477* (2013.01); *A61B 2017/00986* (2013.01); *A61B 2017/0225* (2013.01)

(58) Field of Classification Search
CPC ....... A61B 17/02–17/0293; A61B 1/313–1/32; A61B 2017/0034; A61M 25/09041
See application file for complete search history.

(56) References Cited

U.S. PATENT DOCUMENTS

| | | | | |
|---|---|---|---|---|
| 4,634,421 A | * | 1/1987 | Hegemann | A61F 2/0009 251/7 |
| 4,673,393 A | * | 6/1987 | Suzuki | A61M 39/0606 138/89 |
| 4,715,360 A | * | 12/1987 | Akui | A61B 1/00137 128/912 |
| 5,496,289 A | | 3/1996 | Wenstrom, Jr. | |
| 5,514,133 A | | 5/1996 | Golub et al. | |
| 5,562,688 A | * | 10/1996 | Riza | A61B 17/0469 606/139 |
| 5,643,293 A | * | 7/1997 | Kogasaka | A61B 17/0469 112/169 |
| 5,657,963 A | * | 8/1997 | Hinchliffe | A61B 17/3462 251/149.1 |
| 5,749,892 A | | 5/1998 | Vierra et al. | |
| 5,817,067 A | * | 10/1998 | Tsukada | A61F 2/0018 604/256 |

(Continued)

*Primary Examiner* — Nicholas J Plionis
*Assistant Examiner* — Steven Cotroneo

(57) ABSTRACT

Various devices, systems, and methods are provided for allowing surgical instruments to access a body cavity through an access device, such as a cannula. In one embodiment, a cap can be removably and replaceably coupled to a proximal end of cannula and can have an opening therethrough that communicates with an inner passageway of the cannula. Various surgical elements can be passed through the cap and cannula and into a patient when the cannula is positioned within the patient. The cap can have a side slot formed therein. The slot can be configured to allow surgical elements, such as sutures, to pass through the cap and into the cannula. At least one surgical seal can be in the cap and can be configured to receive surgical elements therethrough.

3 Claims, 8 Drawing Sheets

(56) References Cited

U.S. PATENT DOCUMENTS

| | | | | |
|---|---|---|---|---|
| 5,820,606 A | * | 10/1998 | Davis | A61B 17/3462 604/256 |
| 5,911,714 A | | 6/1999 | Wenstrom, Jr. | |
| 6,210,323 B1 | * | 4/2001 | Gilhuly | A61B 17/02 600/208 |
| 6,267,766 B1 | * | 7/2001 | Burkhart | A61B 17/0401 606/232 |
| 6,564,805 B2 | * | 5/2003 | Garrison | A61B 17/00234 128/898 |
| 7,048,755 B2 | * | 5/2006 | Bonutti | A61B 17/0487 24/122.3 |
| 7,087,041 B2 | * | 8/2006 | von Dyck | A61F 5/442 604/332 |
| 7,163,525 B2 | | 1/2007 | Franer | |
| 8,052,720 B2 | * | 11/2011 | Kuester | A61B 17/7037 606/246 |
| 8,109,910 B2 | * | 2/2012 | Zastawny | A61B 17/3462 604/167.02 |
| 8,333,774 B2 | | 12/2012 | Morrison | |
| 8,430,811 B2 | * | 4/2013 | Hess | A61B 17/3423 600/203 |
| RE44,790 E | | 3/2014 | de la Torre et al. | |
| 8,663,271 B2 | * | 3/2014 | Mantell | A61B 17/3431 604/27 |
| 8,685,063 B2 | * | 4/2014 | Chin | A61B 17/3421 606/265 |
| 8,753,269 B2 | * | 6/2014 | Tabor | A61B 17/3423 600/201 |
| 8,961,407 B2 | | 2/2015 | Piskun et al. | |
| 9,226,817 B2 | | 1/2016 | Dougherty et al. | |
| 9,901,373 B2 | * | 2/2018 | McFarlane | A61M 39/0613 |
| 2003/0092970 A1 | * | 5/2003 | Lee | A61B 17/0231 600/236 |
| 2004/0098050 A1 | * | 5/2004 | Foerster | A61B 17/0401 606/232 |
| 2006/0135977 A1 | * | 6/2006 | Thompson | A61B 17/3462 606/185 |
| 2010/0210912 A1 | * | 8/2010 | Bettuchi | A61B 17/06061 600/201 |
| 2014/0277132 A1 | * | 9/2014 | Sengun | A61B 17/0401 606/232 |
| 2015/0038794 A1 | | 2/2015 | Pattison et al. | |
| 2015/0150595 A1 | | 6/2015 | Pattison et al. | |
| 2016/0015425 A1 | * | 1/2016 | Bolanos | B29C 45/1679 600/204 |
| 2017/0319828 A1 | * | 11/2017 | Doepker | A61B 17/0218 |

* cited by examiner

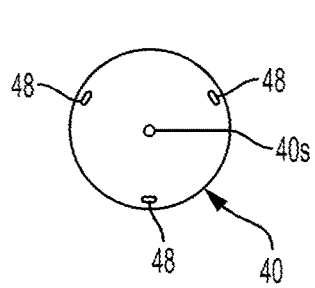 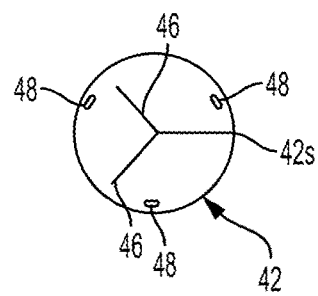 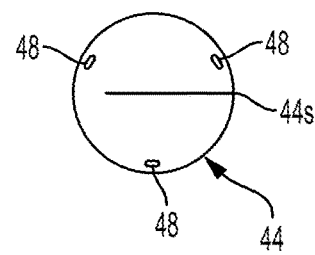
FIG. 3A   FIG. 3B   FIG. 3C
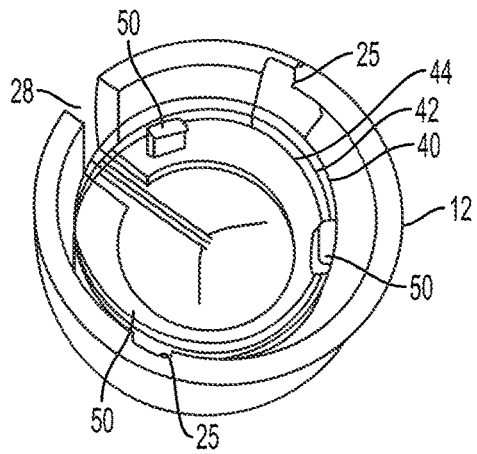
FIG. 4
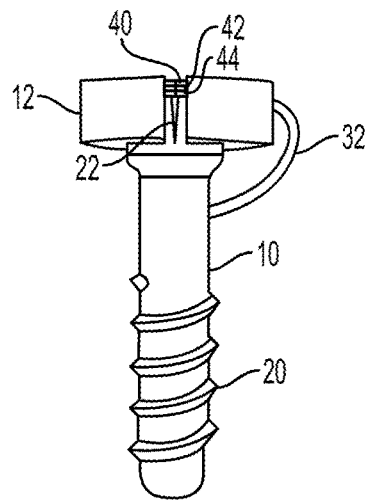
FIG. 5

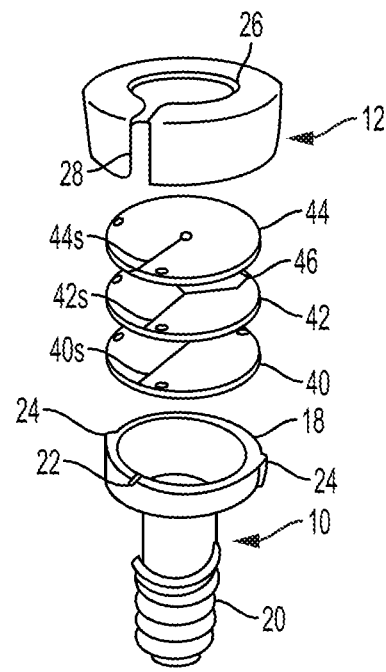
FIG. 6
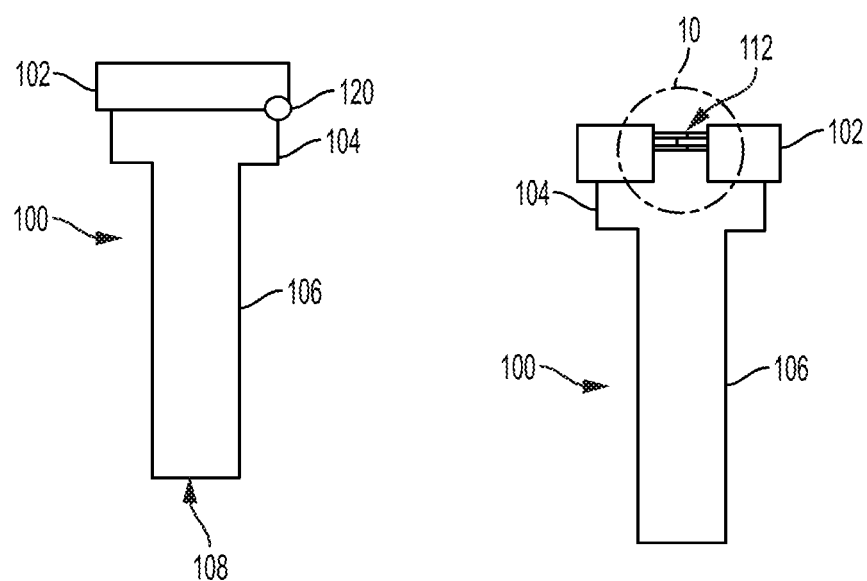
FIG. 7
FIG. 8

US 10,349,929 B2

CANNULA WITH CAP

FIELD

Methods, systems, and devices are provided for allowing surgical instruments to access a body cavity through a cannula.

BACKGROUND

Various surgical operations require access to an inner body cavity of a patient through a cannula. For example, in arthroscopy and laparoscopy, a cannula can be used to provide access to various surgical sites in joints and/or cavities, allowing surgical instruments, sutures, and various other surgical tools to be passed through the cannula. A cannula can also be used to provide positive air and/or water pressure at the surgical site without losing access to the surgical site through use of various seals, such as deformable dams.

While adding seals to the cannula allows pressure to be maintained, the seals can restrict access to various tools through the cannula because the seals can obstruct part or all of the cannula. Various removable dams can be used, but insertion and placement of the dams can cause problems. For example, if sutures extend from a body cavity and out of a cannula, introducing a removable dam to the cannula would either pinch the sutures or require a surgeon to introduce the sutures through an opening in the dam, causing a loss of time and effort during surgery.

Accordingly, there remains a need for improved methods, systems, and devices for allowing surgical instruments to access a body cavity through a cannula.

SUMMARY

Various surgical methods, systems, and devices are provided for allowing surgical instruments to access a body cavity through a cannula.

In one aspect, a surgical system is provided that in one embodiment includes a cannula configured to be positioned in tissue and provide a pathway therethrough. The cannula has an inner passageway extending between open proximal and distal ends thereof. The system also includes a cap configured to be removably and replaceably coupled to the open proximal end of the cannula. The cap has an inner opening that is configured to be in communication with the inner passageway when the cap is removably and replaceably coupled to the open proximal end of the cannula. Surgical instrument can be advanced through the inner opening and into the inner passageway. The cap has a side slot formed in a rim thereof, and the side slot is in communication with the inner opening.

The system can vary in any of a number of ways. For example, the cap can have a sealing element that seals the inner passageway when the cap is removably and replaceably coupled to the open proximal end of the cannula, and the sealing element can be configured to provide a seal around the surgical instrument advanced through the inner opening and into the inner passageway. In at least some embodiments, the sealing element can include a plurality of sealing elements that each have a slot formed therein, and each of the sealing element slots can be aligned with the side slot such that when a suture extends through the inner passageway and through the sealing element slots the suture is configured to move through the sealing element slots and out of the side slot. In another example, when the cap is removably and replaceably coupled to the open proximal end of the cannula, the side slot can be configured to provide a pathway from outside the cap and cannula to within the inner passageway. In yet another example, the rim can be C-shaped. In another example, the cap can be coupled to the cannula via a hinge, and removing the cap from the cannula can include opening the hinge. In yet another example, the cannula can have at least one coupling feature thereon, and the cap can have at least one coupling feature thereon configured to engage the at least one coupling feature of the cannula to couple the cap to the open proximal end of the cannula. In at least some embodiments, the at least one coupling feature of the cannula can be one of male and female, and the at least one coupling feature of the cap can be the other of male and female. In still another example, a proximal end of the cannula can have one or more suture engaging features configured to releasably engage a suture extending through the inner passageway. In another example, the system can also include a suture configured to extend through the inner passageway and the inner opening, and when the cap is removably and replaceably coupled to the open proximal end of the cannula and the suture is extending through the inner passageway and the inner opening, the cap can be configured to be removed from the cannula with the suture passing through the side slot and can remain extending through the inner passageway.

In another embodiment, a surgical system is provided that includes an access device configured to be positioned in tissue and provide a pathway therethrough. The access device has an inner passageway extending therethrough. The system also includes a cap configured to be removably and replaceably coupled to a proximal end of the access device. The cap has an inner opening in communication with the inner passageway of the access device when the cap is removably and replaceably coupled to the proximal end of the access device, and the cap has a slot formed through a sidewall thereof. The slot is configured to allow a surgical element to be at least one of side loaded into the inner opening therethrough and removed from the inner opening by passing therethrough.

The system can have any number of variations. For example, the cap can be configured to be removed from the proximal end of the access device with the surgical element positioned in the inner opening and remain in the inner opening after the cap is removed from the proximal end of the access device. In another example, the surgical element can be a suture. In at least some embodiments, the cap can be configured to be removed from the proximal end of the access device with the suture positioned in the inner opening and in the inner passageway and the suture passing through the slot when the cap is removed from the proximal end of the access device. In yet another example, the cap can be coupled to the proximal end of the access device via a hinge, and removing the cap from the proximal end of the access device can include opening the hinge. In another example, the cap can have a sealing element therein configured to form a seal of the inner passageway of the access device. In at least some embodiments, the sealing element can be configured to seal around a surgical instrument disposed therethrough and passed into the inner passageway of the access device, and the sealing element can be configured to seal the inner passageway when a surgical instrument is not disposed therethrough.

In another aspect, a surgical method is provided that in one embodiment includes positioning a cannula in tissue to form a pathway therethrough such that a surgical instrument can be passed through the tissue by being advanced into a proximal end of the cannula and passed out a distal end of the cannula. The method also includes removing a cap from the proximal end of the cannula such that a surgical element extending through the cannula passes through a slot formed in a sidewall of the cap and remains extending through the cannula after the removal of the cap.

The method can vary in any number of ways. For example, the cap can include a sealing element that forms a seal of an inner passageway of the cannula that extends between the proximal and distal ends thereof, and the removal of the cap can cause loss of the seal of the inner passageway. In another example, the method can include, after removing the cap, re-coupling the cap to the proximal end of the cannula such that the surgical element extending through the cannula passes through the slot and remains extending through the cannula after the re-coupling of the cap. In yet another example, the surgical element can be a suture.

BRIEF DESCRIPTION OF DRAWINGS

This invention will be more fully understood from the following detailed description taken in conjunction with the accompanying drawings, in which:

FIG. 3A is a top view of a surgical seal of the cap of FIG. 1;

FIG. 3B is a top view of another surgical seal of the cap of FIG. 1;

FIG. 3C is a top view of yet another surgical seal of the cap of FIG. 1;

FIG. 4 is a perspective view of a bottom surface of the cap of FIG. 1 with the surgical seals of FIGS. 3A, 3B, and 3C;

FIG. 5 is a side view of the cannula and cap of FIG. 1 with the surgical seals of FIGS. 3A, 3B, and 3C;

FIG. 6 is an exploded perspective view of the cannula, cap, and surgical seals of FIG. 5;

FIG. 7 is a side schematic view of another embodiment of a cannula with a removable cap;

FIG. 8 is another side schematic view of the cannula and cap of FIG. 7;

DETAILED DESCRIPTION

Figure 1:
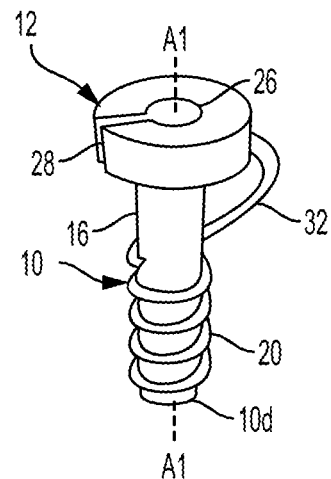
FIG. 1 is a perspective view of one embodiment of a cannula with a removable cap.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various devices, systems, and methods are provided for allowing surgical instruments to access a body cavity through an access device, such as a cannula. In an exemplary embodiment, a cap can be removably and replaceably coupled to a proximal end of a cannula and can have an opening therethrough that communicates with an inner passageway extending through the cannula. Various surgical elements can be passed through the cap and cannula and into a patient when the cannula is positioned within the patient. The cap can have a side slot formed therein. The slot can be configured to allow surgical elements, such as sutures, to pass through the cap and into the cannula. The slot can be configured to allow the surgical elements to move through the slot during opening and closing of the cap such that the surgical elements can remain in the passageway of the cannula during the opening (e.g., removing the cap from the cannula's proximal end) and closing (e.g., putting or replacing the cap on the cannula's proximal end). The cap may thus be quickly and efficiently opened and closed without the surgical elements having to be repositioned and/or reinserted every time the cap is opened or closed. At least one surgical seal can be in the cap and can be configured to receive surgical elements therethrough. The at least one surgical seal can have an opening that aligns with the side slot and can be configured to allow the surgical elements to be passed therethrough. The opening being aligned with the side slot may simplify passing of the surgical elements through the at least one surgical seal.

Figure 2:
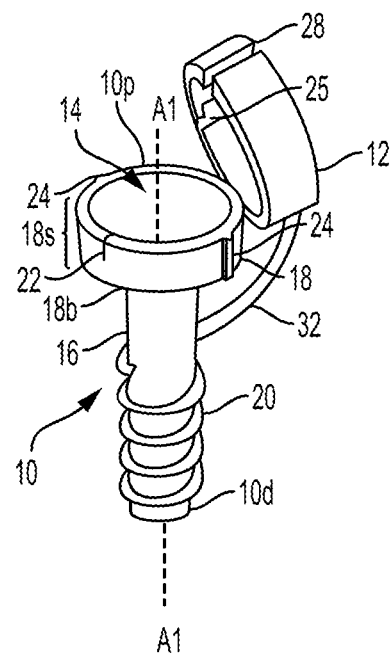
FIG. 2 is a perspective view of the cannula of FIG. 1 with the cap removed.

FIGS. 1, 2, and 4-6 illustrate one embodiment of an access device in the form of a cannula 10. The cannula 10 has a distal end 10d and a proximal end 10p. An inner passageway 14 extends longitudinally through the cannula 10 along a longitudinal axis A1 between the distal and proximal ends 10d, 10p. The passageway 14 is configured to allow passage of surgical elements therethrough, such as sutures and surgical instruments. The cannula 10 has a head 18 and an elongate body 16 extending distally therefrom. The head 18 is at the proximal end 10p of the cannula 10 and is configured to receive the cap 12 thereon. FIGS. 1 and 5 illustrate the cannula 10 with the cap 12 attached thereto, e.g., with the cap 12 on. FIG. 2 illustrates the cannula 10 with the cap 12 removed therefrom, e.g., with the cap 12 off. The cannula 10 can have a variety of sizes and be made from a variety of materials. For example, the cannula 10 can have a diameter of about 10 mm and can be made of plastic.

The elongate body 16 has a tissue-engaging feature thereon in the form of threading 20 extending therealong. The threading 20 is configured to allow the cannula 10 to thread into a body of a patient by engaging tissue of the patient, which may help introduction of the cannula 10 into the patient's body and/or help the cannula 10 stay in position in the patient's tissue once threaded therein. The threading 20 can extend along an entire length of the body 16 or along a partial length thereof, as in this illustrated embodiment in which the threading 20 is only on a distal portion of the body 16. Other examples of tissue-engaging features include ribs and a textured surface.

The head 18 has a circular shape, although the head 18 can have other shapes. The head 18 has a larger diameter than the elongate body 16, which may facilitate positioning of the cannula 10 in tissue by the head 18 serving as a stop to help to prevent the cannula 10 from slipping distally or moving entirely into the patient's body through the smaller-diameter opening in the patient's tissue in which the elongate body 16 is positioned. The head 18 has a side wall 18s that extends substantially parallel to the longitudinal axis A1 and is configured to receive the cap 12 therearound. A person skilled in the art will appreciate that the side wall 18s may not be precisely parallel to the longitudinal axis A1 but nevertheless be considered to be substantially parallel thereto for any of a variety of reasons, such as manufacturing tolerances and sensitivity of measurement devices. The head 18 has a distal or lower surface 18b that extends between the side wall 18s of the head 18 and the elongate body 16. The lower surface 18b is configured to act as a stop surface that abuts against a patient, e.g., against the patient's skin, to help prevent the cannula 10 from slipping or moving entirely into the patient's body as discussed above.

The head 18 has one or more suture-engaging elements 22 that are each configured to receive a suture therein. Each suture-engaging element 22 is configured to receive one suture therein and can, depending on the size of the suture-engaging element 22 and the size of the sutures, be configured to receive multiple sutures therein. The head 18 has one suture-engaging element 22 in this illustrated embodiment, and the suture-engaging element 22 is in the form of a notch formed in the side wall 18s of the head 18. The suture-engaging element 22 is configured to receive and crimp a suture therein. In this way, a suture extending through the elongate body 16 can have a proximal tail thereof held in the suture-engaging element 22, where the suture may be held at a desired tension and/or be out of the way for other surgical elements introduced through the cannula 10. Other examples of suture-engaging elements include protrusions around which a suture can be wrapped or tied and clips configured to clip a suture therein.

The head 18 has one or more mating elements 24 configured to facilitate mating of the cap 12 to the cannula 10. The mating elements 24 in this illustrated embodiment are male members on an exterior surface of the head 18 configured to be received in corresponding female mating elements 25 on an interior surface of the cap 12. The cannula mating elements 24 and cap mating elements 25 can be configured to cooperate to prevent rotational movement of the cap 12 about the cannula 10, e.g., about the head 18 thereof, when the mating elements 24, 25 are mated together. Preventing this rotational movement may help prevent the cap 12 from undesirably moving during introduction or removal of surgical elements from the cannula 10 when the cap 12 is attached thereto and/or may help a user recognize when the cap 12 is fully mated to the cannula 10. The cannula mating elements 24 and cap mating elements 25 can be configured to align the cap 12 in a predetermined orientation relative to the cannula 10 when mated thereto, which may ensure that at least one of the cannula's one or more suture-engaging elements 22 is aligned with the cap's slot 28 when the cap 12 is on the head 18. In other embodiments, a cannula can include one or more female mating elements and a cap can include one or more male mating elements.

The cap 12 has a shape corresponding to the shape of the cannula's head 18, which is circular in the illustrated embodiment. The cap 12 is configured to removably and replaceably couple to the head 18 of the cannula 10. An inner opening 26 is formed through the cap 12. The opening 26 is configured to align with the passageway 14 of the cannula 10 when the cap 12 is on the cannula 10 to allow surgical elements to pass through both the opening 26 and passageway 14. The opening 26 is circular, but any shape can be used. A slot 28 is formed in the cap 12 and extends through a side wall of the cap 12 and along a proximal surface of the cap 12 to the opening 26. The cap 12 thus has a C-shape and a discontinuous outer perimeter. The head 18 has a continuous outer perimeter, as shown in FIGS. 2 and 6. The slot 28 is configured to allow surgical elements, such as sutures, to pass therethrough such that the surgical elements can extend through the passageway 14 to the opening 26 and be passed into the slot 28 without opening the cap 12, e.g., without removing the cap 12 from the cannula 10. The slot 28 being aligned with at least one of the one or more suture-engaging elements 22 when the cap 12 is on the cannula 10, as shown in FIG. 5, may allow quick and easy engagement of the surgical elements with the aligned at least one of the one or more suture-engaging elements 22.

The cap 12 is attached to the cannula 10 via an attachment mechanism 32. The attachment mechanism 32 in this illustrated embodiment is a tether, but other attachment mechanisms are possible, such as a hinge, a string, a buckle, etc. The attachment mechanism 32 is configured to facilitate manual removal and replacement of the cap 12. The attachment mechanism 32 is configured to allow the cap 12 to remain connected to the cannula 10 when the cap 12 is off the cannula's proximal end 10p, which may help prevent loss of the cap 12 and/or speed its replacement on the cannula 10 because a user need not fumble to locate the cap 12 during surgery.

The cap 12 includes one or more sealing mechanisms 40, 42, 44, such as deformable dam seals as illustrated in FIGS.

3A-4 and 6. The one or more sealing mechanisms 40, 42, 44 are configured to seal against the passage of air and/or liquid therethrough. Pressure may thus be maintained in a body cavity and/or joint over which the sealing mechanisms 40, 42, 44 are providing a seal. While the cap 12 in this illustrated embodiment includes three sealing mechanisms 40, 42, 44, any number of sealing mechanisms can be used. In an exemplary embodiment, at least two sealing mechanisms are used, which may help maintain a seal when a surgical element extends therethrough. The sealing mechanisms 40, 42, 44 are arranged in a vertical stack in the cap 12, as shown in FIGS. 4 and 6.

At least one slot 40s, 42s, 44s is formed in each of the sealing mechanisms 40, 42, 44, respectively, that is configured to allow surgical elements to pass therethrough. The slots 40s, 42s, 44s are aligned with each other in a vertical direction, as shown in FIGS. 4 and 5, which may facilitate passage of surgical elements therethrough. The slots 40s, 42s, 44s are also aligned with the slot 28 of the cap 12, as shown in FIGS. 4 and 5, which may facilitate movement of surgical elements through the slot 28 during opening and closing of the cap 12. Each of the slots 40s, 42s, 44s is different from one another, which may help maintain a seal when a surgical element extends therethrough. The proximal and distal sealing mechanism's slots 40s, 44s each have a linear or straight line shape, but the distal one of the linear slots 44s is longer than the proximal one of the linear slots 40s. The middle sealing mechanism's slot 42s has a "Y" shape with arms 46 extending angularly from a linear or straight line portion of the slots 42s. In other embodiments, the slots 40s, 42s, 44s can be the same as one another.

A plurality of seal retention features 48 are formed on each of the sealing mechanisms 40, 42, 44. The seal retention features 48 are configured to facilitate attachment of the sealing mechanisms 40, 42, 44 to the cap 12. The sealing mechanisms 40, 42, 44 are thus removable and replaceable from the cannula 10 with the cap 12. The seal retention features 48 in this illustrated embodiment are openings formed through each of the sealing mechanisms 40, 42, 44 through which corresponding seal capture features 50, e.g., protrusions, tabs, etc., of the cap 12 are received, but other variations are possible, such as hooks, clasps, buckles, etc. The seal capture features 50 in this illustrated embodiment are tabs projecting from an interior surface of the cap 12. The seal capture features 50 are configured to be inserted into the seal retention features 48 of the sealing mechanisms 40, 42, 44 such that the sealing mechanisms 40, 42, 44 are retained by frictional force in the cap 12.

Figure 9:
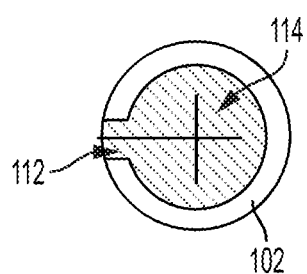
FIG. 9 is a top schematic view of the cannula and cap of FIG. 7.
Figure 10:
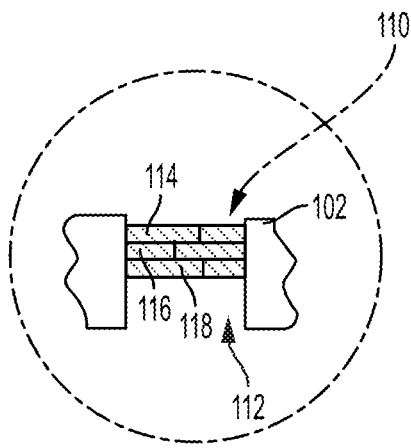
FIG. 10 is a portion of the cap of FIG. 8.

FIGS. 7-10 illustrate another embodiment of an access device in the form of a cannula 100 with a cap 102 configured to be selectively positioned on and off the cannula's proximal end. The cannula 100 is generally configured and used similar to the cannula 10 of FIGS. 1, 2, 5, and 6, e.g., has a head 104 and an elongate body 106 extending distally from the head 104, one or more mating elements (obscured in FIGS. 7-9) configured to mate to corresponding mating elements (also obscured in FIGS. 7-9) of the cap 102, and a passageway 108. The cannula 100 in this illustrated embodiment does not include a tissue-engaging feature but can include a tissue-engaging feature, as discussed above. The cannula 100 in this illustrated embodiment also does not include a suture-engaging element but can include one or more suture-engaging elements, as discussed above. The cap 102 is generally configured and used similar to the cap 12 of FIGS. 1, 2, and 4-6, e.g., has an inner opening 110, a slot 112, and one or more sealing mechanisms 114, 116, 118. As shown in FIGS. 8 and 10, the sealing mechanisms 114, 116, 118 are arranged in the cap 102 in a vertical stack. Slots of each of the sealing mechanisms 114, 116, 118 are offset radially from one another at the cap's slot 112, as shown in FIGS. 8 and 10, which may help maintain a seal when a surgical element extends therethrough. In this illustrated embodiment, an attachment mechanism 120 in the form of a hinge attaches the cap 112 to the cannula 110. FIGS. 7-9 show the cannula 100 with the cap 102 thereon.

Figure 11:
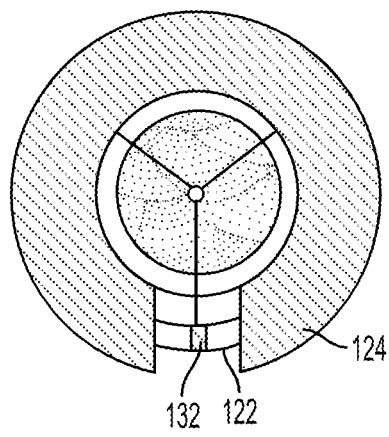
FIG. 11 is a top view of another embodiment of a cannula with a removable cap thereon.
Figure 12:
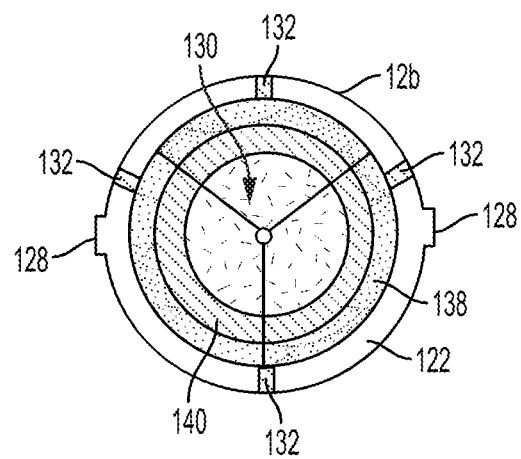
FIG. 12 is a top view of the cannula of FIG. 11 with the cap removed therefrom.

FIGS. 11 and 12 illustrate another embodiment of an access device in the form of a cannula 122 with a cap 124 configured to be selectively positioned on and off the cannula's proximal end. FIG. 11 shows the cap 124 on the cannula 122. FIG. 12 shows the cap 124 off the cannula 122. In this illustrated embodiment, the cap 124 is not attached to the cannula 122 with an attachment mechanism, but as mentioned above, an attachment mechanism can be used. The cannula 122 is generally configured and used similar to the cannula 10 of FIGS. 1, 2, 5, and 6, e.g., has a head 126 and an elongate body (obscured in FIGS. 11 and 12) extending distally from the head 126, one or more mating elements 128 configured to mate to corresponding mating elements (obscured in FIG. 11) of the cap 124, a passageway 130, and one or more suture-engaging elements 132. The cannula 122 can include a tissue-engaging feature, as discussed above. The cap 124 is generally configured and used similar to the cap 12 of FIGS. 1, 2, and 4-6, e.g., has an inner opening 134 and a slot 136. In this illustrated embodiment, the cannula 122 includes one or more sealing mechanisms 138, 140 which are two vertically stacked seals in this illustrated embodiment. The proximal one of the sealing mechanisms 138 has a linear or straight line slot, and the distal one of the sealing mechanisms 140 has a "Y" shaped slot.

Figure 13:
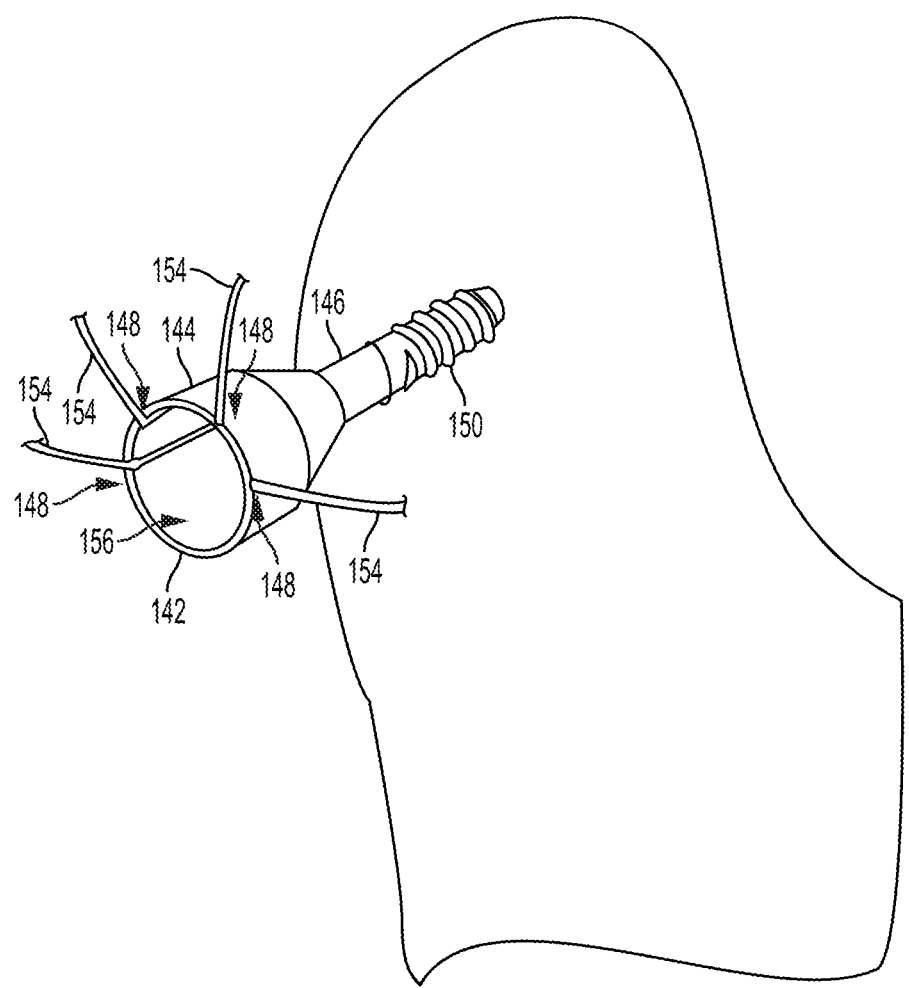
FIG. 13 is a schematic perspective view of another embodiment of a cannula positioned in a body of a patient.

FIG. 13 illustrates another embodiment of an access device in the form of a cannula 142 configured to have a cap selectively positioned on and off the cannula's proximal end. The cap is not illustrated in FIG. 13 but can generally be configured and used similar to the cap 12 of FIGS. 1, 2, 5, and 6, although the cap is not attached to the cannula 142 with an attachment mechanism in this illustrated embodiment. The cannula 142 is generally configured and used similar to the cannula 10 of FIGS. 1, 2, and 4-6, e.g., has a head 144 and an elongate body 146 extending distally from the head 144, a passageway 156, one or more suture-engaging elements 148, and a tissue-engaging feature 150 in the form of threading on a distal portion of the elongate body 146. The cannula 142 in this illustrated embodiment does not include mating elements configured to mate to corresponding mating elements of the cap, but can include such mating elements as discussed above. FIG. 13 illustrates the elongate body 146 positioned in a shoulder of a patient 152 with the threading 150 fully disposed within the patient 152 and the head 144 outside of the patient 152. FIG. 13 also illustrates four sutures 154 extending from inside the patient's body, through the passageway 156, and received in the suture-engaging elements 148.

One embodiment of a method of using a cannula with a removable and replaceable cap is illustrated in FIGS. 14-17. Although the method of FIGS. 14-17 is illustrated with respect to a cannula 10' and the cap 12 of FIGS. 1, 2, and 4-6, any of the cannulas and caps described herein can be similarly used. The cannula 10' is generally configured and used similar to the cannula 10 of FIGS. 1, 2, 5, and 6 except that the cannula 10' of FIGS. 14-17 has four suture-engaging elements 22' instead of one suture-engaging element 22.

Figure 14:
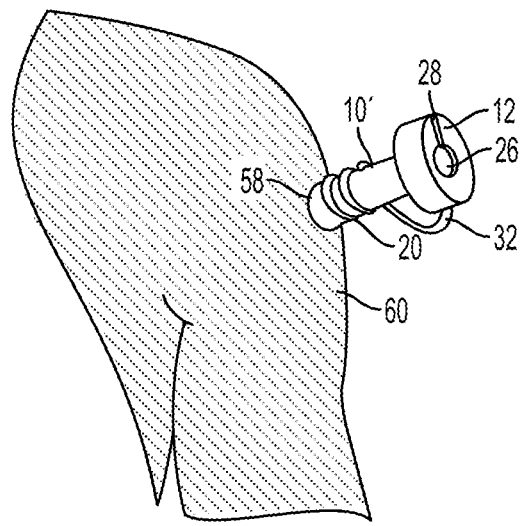
FIG. 14 is a perspective view of another embodiment of a cannula with a removable cap thereon positioned in a patient.

As shown in FIG. 14, the cannula 10' has been advanced through an incision 58 and is positioned in tissue 60 at a shoulder of a patient. The incision 58 is pre-formed in the patient using any of a variety of techniques, as will be appreciated by a person skilled in the art. In an exemplary embodiment, the cap 12 is on the cannula 10' during the advancement of the cannula 10' through the incision 58 to facilitate handling of the system including the cannula 10' and cap 12.

Figure 15:
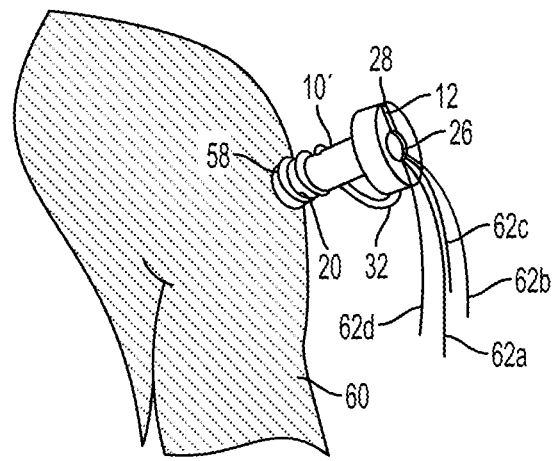
FIG. 15 is a perspective view of the cannula and cap of FIG. 15 with sutures extending therefrom.

FIG. 15 illustrates a plurality of sutures 62a, 62b, 62c, 62d extending from within the patient, through the tissue 60, and through the cannula's passageway 14 and the cap's opening 26 with trailing proximal ends of the sutures 62a, 62b, 62c, 62d located outside of the patient. The sutures 62a, 62b, 62c, 62d pass through the sealing mechanisms 40, 42, 44 in the cap 12, and the sealing mechanisms 40, 42, 44 maintain a seal across the passageway 14.

Figure 16:
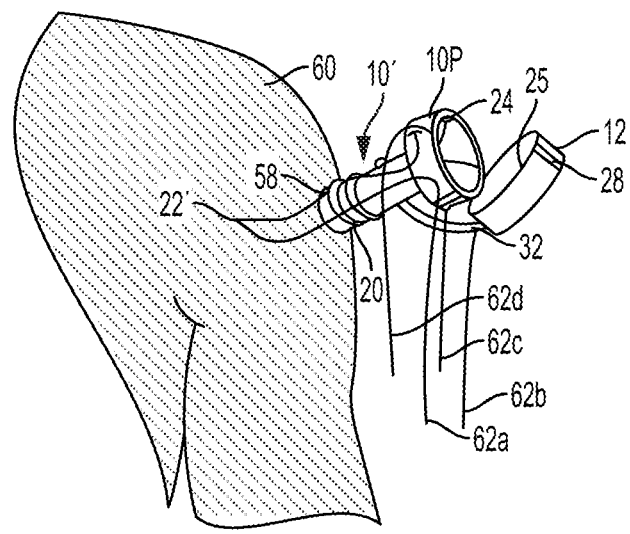
FIG. 16 is a perspective view of the cannula of FIG. 15 with the cap removed.

The cap 12 can be removed from the proximal end of the cannula 10' such that the cap 12 is in the open position and remains attached to the cannula 10' via the attachment mechanism 32. The cap 12 may be removed for any of a variety of reasons while the cannula 10' is positioned in the patient, as will be appreciated by a person skilled in the art, such as to pass a graft or a surgical instrument through the cannula 10' that is too large to pass through the cap's opening 26. While the cap 12 is being opened, the sutures 62a, 62b, 62c, 62d can pass through the slots 40s, 42s, 44s of the sealing mechanisms 40, 42, 44 and through the slot 28 in the cap 12. In this way, the sutures 62a, 62b, 62c, 62d can remain extending through the cannula during and after removal of the cap 12 from the cannula's proximal end 10p, as shown in FIG. 16. As illustrated in FIG. 16, when the cap 12 is in the open position, the one or more suture-engaging elements 22' of the cannula 10' can receive the sutures 62a, 62b, 62c, 62d to secure the sutures 62a, 62b, 62c, 62d in place and prevent dislodging or loss of the sutures 62a, 62b, 62c, 62d from a desired position when the cap 12 is open. For example, if an additional surgical element, such as a surgical instrument, is inserted through the open cannula 10', the sutures 62a, 62b, 62c, 62d can remain in place without risking entanglement or dislodgement by the additional surgical element. In this illustrated embodiment, each one of the suture-engaging elements 22' engages one of the sutures 62a, 62b, 62c, 62d mentioned above, multiple sutures may be receivable in a single suture-engaging element 22'.

As the cap 12 is opened, the sealing mechanisms 40, 42, 44 will remain in the cap 12 such that the seal across the passageway 14 will be at least partially lost and pressure within the patient will also be at least partially lost. This loss of the seal may be an acceptable consequence of removing the cap 12 to, e.g., allow larger items to be passed through the cannula's passageway 14 since the passage of these items typically takes a brief amount of time, e.g., in a range of about 5 to 10 seconds. Without a removable cap, larger items would have to be passed through sealing mechanisms sealing a cannula, which can be difficult or impossible given the size and pliability of the sealing mechanisms. In at least some instances, the cannula would have to be removed from the patient to allow the passage of the larger items and subsequently repositioned in the patient. The removable cap 12 may thus save time and/or help prevent damaging the items being introduced into or removed from the patient.

Figure 17:
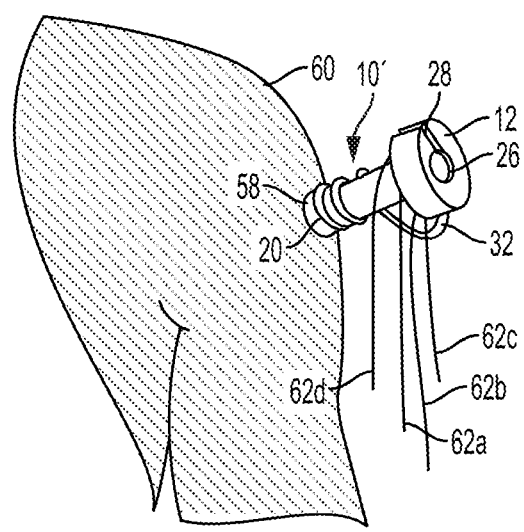
FIG. 17 is a perspective view of the cannula of FIG. 16 with the cap replaced on the cannula.

With the sutures 62a, 62b, 62c, 62d engaged by the suture-engaging elements 22', the cap 12 can be closed, as illustrated in FIG. 17. When the cap 12 moved back to the closed position, the cap 12 re-couples to the proximal end of the cannula 10' and re-seals the passageway 14. The sutures 62a, 62b, 62c, 62d remain in the suture-engaging elements 22' and are now also held in place by the cap 12, which may provide more robust securing of the sutures 62a, 62b, 62c, 62d in place than use of the suture-engaging elements 22' alone. The cap 12 closure process may thus be fast and simple, avoiding additional steps required to pass the sutures 62a, 62b, 62c, 62d through the sealing mechanisms 40, 42, 44 while still allowing the cannula 10' to have a seal across its passageway 14 and allow positive pressure in the patient.

Surgical elements can either pass through the cannula one at a time or simultaneously. For example, a user can remove the cap 12 from its position in FIG. 14, insert a surgical instrument through the cannula 10' to perform various operations within the patient, remove the instrument, and replace the cap 12 to reseal the passageway 14. The sutures 62a, 62b, 62c, 62d can either remain extending through the cannula 10', as shown in FIG. 16, or can be removed from the cannula 10' during use of the surgical instrument.

FIGS. 18-21 illustrate another embodiment of a method of using a cannula with a removable and replaceable cap. Although the method of FIGS. 18-21 is illustrated with respect to a cannula 100 and the cap 102 of FIGS. 7-10, any of the cannulas and caps described herein can be similarly used.

Figure 18:
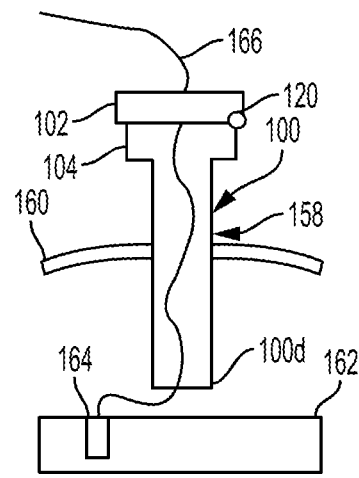
FIG. 18 is side, partially cross-sectioned, partially transparent schematic view of the cannula and cap of FIG. 7 positioned in skin with a suture extending through the cannula and cap.

As shown in FIG. 18, the cannula 100 has been advanced through an incision 158 in skin 160 of a patient such that a distal end 100d of the cannula 100 is positioned within the patient proximal to bone 162 and such that the head 104 with the cap 102 thereon is outside of the patient. The incision 158 is pre-formed in the patient using any of a variety of techniques, as will be appreciated by a person skilled in the art. In an exemplary embodiment, the cap 102 is on the cannula 100 during the advancement of the cannula 100 through the incision 158 to facilitate handling of the system including the cannula 100 and cap 102. A suture anchor 164 has been driven into the bone 162, which can be accomplished in any of a variety of ways, as will be appreciated by a person skilled in the art. A suture 166 coupled to the suture anchor 164 has been passed through the passageway 108 of the cannula 100 and the opening 110 of the cap 102 such that a trailing proximal end of the suture 166 is located outside of the patient and proximal to the cannula 100 and cap 102, which can be accomplished in any of a variety of ways, as will be appreciated by a person skilled in the art.

Figure 19:
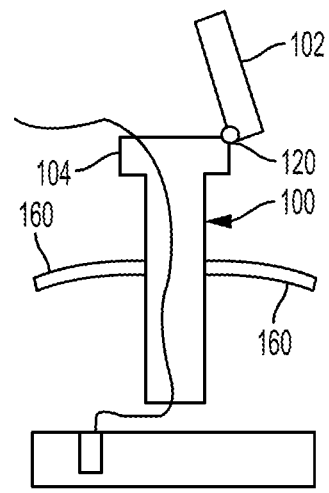
FIG. 19 is a side, partially cross-sectioned, partially transparent schematic view of the cannula and cap of FIG. 18 with the cap removed therefrom.

The cap 102 can be removed from the cannula 100 through hinged movement at the hinge 120 such that the cap 102 is off the cannula 100, as shown in FIG. 19. During the removal of the cap 102, the suture 166 will slide through the slots of the sealing mechanisms 114, 116, 118 and through the slot 112 of the cap 102. The cap 102 in the open position remains attached to the cannula 100 via the attachment mechanism 120.

Figure 20:
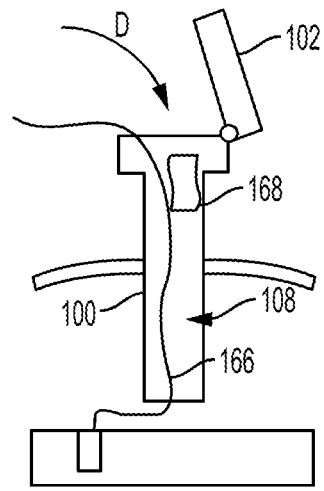
FIG. 20 is a side, partially cross-sectioned, partially transparent schematic view of the cannula and cap of FIG. 19 with a graft being passed through the cannula.
Figure 21:
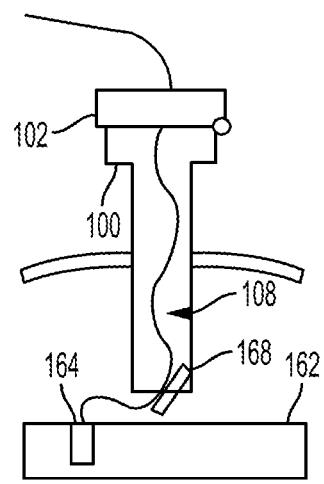
FIG. 21 is a side, partially cross-sectioned, partially transparent schematic view of the cannula and cap of FIG. 20 with the cap replaced on the cannula.

With the cap 102 removed from the cannula 100, an item such as a graft 168 can be advanced distally D into the cannula's passageway 108, as shown in FIG. 20. The graft 168 is larger than the opening 110 in the cap 102 but smaller than the passageway 108 such that removal of the cap 102 allows the graft 168 to be passed into the cannula 100. Once the graft 168 is located within the cannula's passageway 108 or after the graft 168 has been advanced through the passageway 108 and out the distal end 100d of the cannula 100, the cap 102 can be replaced onto the cannula 100, as shown in FIG. 21. During the replacement of the cap 102, the suture 166 can pass through the slots of the sealing mechanisms 114, 116, 118 and through the slot 112 of the cap 102. In this illustrated embodiment, the graft 168 is within the passageway 108 when the cap 102 is put back on the cannula 100, which may allow the sealing provided by the cap 102 to be lost for less time than would be needed to fully pass the graft

168 through the cannula 100 before replacing the cap 102 on the cannula 100. The surgical procedure may then continue to secure the graft 168 to the bone 162 using the suture 166 and suture anchor 164, as will be appreciated by a person skilled in the art.

A person skilled in the art will appreciate that the implementations described herein have application in conventional minimally-invasive and open surgical instrumentation as well application in robotic-assisted surgery.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
   positioning a cannula in tissue to form a pathway therethrough such that a surgical instrument can be passed through the tissue by being advanced into a proximal end of the cannula and passed out a distal end of the cannula; and
   removing a cap from the proximal end of the cannula such that a surgical element extending through the cannula and through a central opening of the cap passes through a slot formed in a sidewall of the cap and remains extending through the cannula after the removal of the cap, the cap including a sealing element that forms a seal of an inner passageway of the cannula that extends between the proximal and distal ends thereof, and the removal of the cap causing loss of the seal of the inner passageway.

2. The method of claim 1, further comprising, after removing the cap, re-coupling the cap to the proximal end of the cannula such that the surgical element extending through the cannula passes through the slot and remains extending through the cannula after the re-coupling of the cap.

3. A surgical method, comprising:
   positioning a cannula in tissue to form a pathway therethrough such that a surgical instrument can be passed through the tissue by being advanced into a proximal end of the cannula and passed out a distal end of the cannula;
   removing a cap from the proximal end of the cannula such that a surgical element extending through the cannula and through a central opening of the cap passes through a slot formed in a sidewall of the cap and remains extending through the cannula after the removal of the cap; and
   after removing the cap, re-coupling the cap to the proximal end of the cannula such that the surgical element extending through the cannula passes through the slot and remains extending through the cannula after the re-coupling of the cap.

* * * * *